(12) United States Patent
Duckert

(10) Patent No.: US 7,792,689 B2
(45) Date of Patent: Sep. 7, 2010

(54) METHOD AND SYSTEM FOR REMOTELY ADMINISTERING A DIURETIC THERAPY

(75) Inventor: David Wayne Duckert, Menomonee Falls, WI (US)

(73) Assignee: General Electric Company, Scehenctady, NY (US)

( * ) Notice: Subject to any disclaimer, the term of this patent is extended or adjusted under 35 U.S.C. 154(b) by 642 days.

(21) Appl. No.: 11/673,935

(22) Filed: Feb. 12, 2007

(65) Prior Publication Data

US 2008/0195414 A1 Aug. 14, 2008

(51) Int. Cl.
*G06Q 10/00* (2006.01)
(52) U.S. Cl. .............................................. 705/3; 705/2
(58) Field of Classification Search ................ 705/2–4; 600/300–301
See application file for complete search history.

(56) References Cited

U.S. PATENT DOCUMENTS

| 6,014,626 | A  | * | 1/2000  | Cohen ........................ 704/275 |
| 6,980,958 | B1 |   | 2/2007  | Surwit et al. |
| 2002/0194221 | A1 | * | 12/2002 | Strong et al. ................ 707/513 |
| 2005/0136130 | A1 | * | 6/2005  | Lang ........................... 424/638 |
| 2005/0191716 | A1 |   | 9/2005  | Surwit et al. |
| 2007/0162090 | A1 | * | 7/2007  | Penner ........................ 607/60 |

\* cited by examiner

*Primary Examiner*—Vivek D Koppikar
(74) *Attorney, Agent, or Firm*—Andrus, Sceales, Starke & Sawall, LLP

(57) ABSTRACT

A diuretic titration system is disclosed herein. The diuretic titration system includes a server having an algorithm, a communication device operatively connected to the server, and a monitoring device operatively connected to the server. The algorithm is configured to evaluate input from the communication device and/or the monitoring device in order to provide a diuretic dosage recommendation for a remotely located patient. A corresponding method for monitoring and regulating the dosage of a diuretic medication administered to a remotely located patient is also disclosed.

18 Claims, 3 Drawing Sheets

METHOD AND SYSTEM FOR REMOTELY ADMINISTERING A DIURETIC THERAPY

FIELD OF THE INVENTION

This disclosure relates generally to a method and system for administering a diuretic therapy to a remotely located patient.

BACKGROUND OF THE INVENTION

A diuretic is substance that elevates the rate of urine excretion. Diuretics are commonly used to treat conditions such as heart failure, liver cirrhosis, hypertension and kidney diseases. As an example, it is well known that congestive heart failure (CHF) can produce edema which is the swelling of an organ or tissue due to the accumulation of intercellular fluid. Diuretics can therefore be administered to reduce the pathological edema by causing sodium and water loss through the urine.

The process of gradually adjusting the dosage of a medication until the desired effect is achieved is referred to as "titration". Diuretic medications are particularly difficult to titrate because the dosage must frequently be adjusted based on criteria such as the patient's activity level, diet and overall health, and the dosage levels of other administered medications. This is particularly problematic in the field of home healthcare wherein the patient generally receives less direct supervision.

BRIEF DESCRIPTION OF THE INVENTION

The above-mentioned shortcomings, disadvantages and problems are addressed herein which will be understood by reading and understanding the following specification.

In an embodiment, a diuretic titration system includes a server having an algorithm, a communication device operatively connected to the server, and a monitoring device operatively connected to the server. The algorithm is configured to evaluate input from the communication device and/or the monitoring device in order to provide a diuretic dosage recommendation for a remotely located patient.

In another embodiment, a diuretic titration system includes a server having an algorithm, a communication device operatively connected to the server, a monitoring device operatively connected to the server, an electronic medical record transferable to the algorithm, and an evidence based guideline transferable to the algorithm. The algorithm is configured to evaluate input from the communication device, the monitoring device, the electronic medical record, and/or the evidence based guideline in order to provide a diuretic dosage recommendation for a remotely located patient.

In another embodiment, a method for monitoring and regulating the dosage of a diuretic medication administered to a remotely located patient includes obtaining information pertaining to the remotely located patient, transmitting the information to a server, implementing the server to evaluate the information and provide a diuretic dosage recommendation for a the remotely located patient, and conveying the diuretic dosage recommendation to the remotely located patient.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
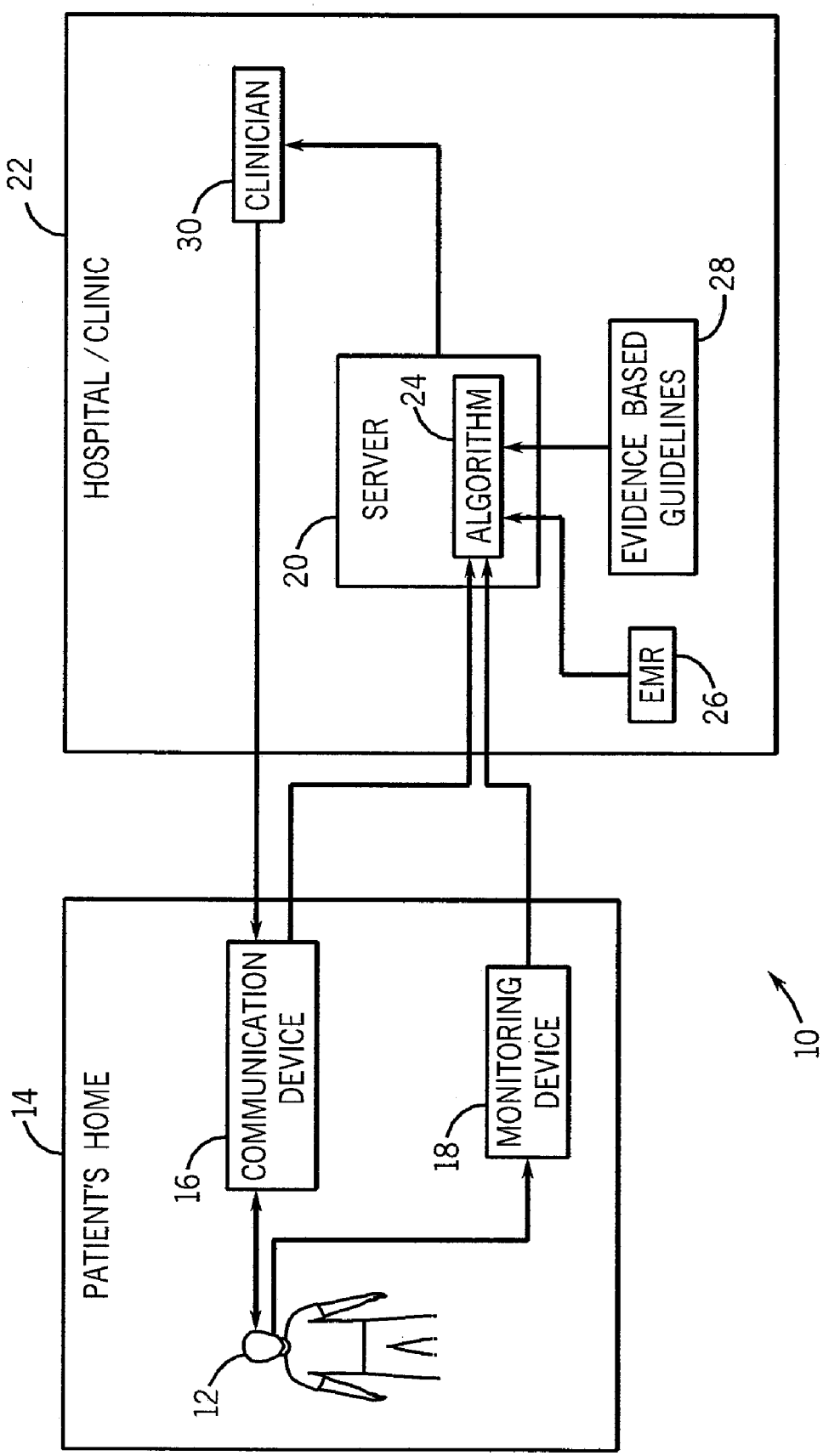
FIG. 1 is a schematic diagram illustrating a diuretic titration system.

Referring to FIG. 1, a diuretic titration system 10 is shown. The diuretic titration system 10 will hereinafter be described in accordance with an exemplary embodiment wherein the diuretic titration system 10 is configured to monitor and regulate the dosage of a remotely located patient 12 being treated in their home 14. It should, however, be appreciated that the diuretic titration system 10 may be implemented for any application wherein a diuretic medication is being remotely administered, monitored and/or regulated. For purposes of this disclosure, the term "remotely located patient" may be defined to include any patient being treated or cared for outside a conventional hospital facility.

The diuretic titration system 10 includes a communication device 16 and a monitoring device 18 disposed within the patient's home 14. The diuretic titration system 10 also includes a server 20 disposed in a hospital or clinic 22. For purposes of this disclosure, a "server" may be defined to include any remotely accessible device comprising a processor. The server 20 is remotely connected to the communication device 16 and the monitoring device 18 in a conventional manner. The server 20 includes an algorithm 24 adapted to receive input from the communication device 16, the monitoring device 18, any electronic medical records (EMR) 26, and/or the evidence based guidelines 28. The algorithm 24 is also adapted to transmit output to the communication device 16 in order to communicate with the patient 12. A clinician 30 may optionally review any information transmitted from the algorithm 24 to the communication device 16 as a precautionary measure.

The communication device 16 may include any device adapted to transfer information to and/or receive data from the patient 12 such as, for example, a telephone, a computer, a personal digital assistant (PDA), etc. According to one embodiment, the communication device 16 includes a telephone comprising interactive voice response (IVR) technology. IVR allows a user to select options from a voice menu and thereby interact with a computer via a telephone system. IVR systems generally play a pre-recorded voice prompt to which the user responds by pressing a number on a telephone keypad.

In a non-limiting manner, an exemplary IVR telephone system may be programmed to ask one or more of the following questions: is the patient experiencing a shortness of breath?; is the patient experiencing any swelling?; does the patient have a rash?; is the patient experiencing hearing loss?; has the patient consumed any foods or beverages with a high sodium content? Following each individual inquiry, the patient 12 may, for example, reply in the affirmative by pressing the number "1" on the telephone keypad, and may reply in the negative by pressing the number "2" on the telephone keypad. Any information input into the communication device 16 by the patient 12 is transferable to the server 20.

The monitoring device 18 is operatively connectable to the patient 12. The monitoring device 18 may include, for example, pressure sensors adapted to weigh the patient 12 and/or motion sensors adapted to monitor patient activity level. The monitoring device 18 may also include a bioimpedance device adapted to estimate the patient's water content. Any data recorded by the monitoring device 18 is transferable to the server 20.

The electronic medical record (EMR) 26 contains medical information pertaining to the patient 12. EMR data relevant to a dosage recommendation for a diuretic medication may include, for example, the patient's diagnosis; the currently prescribed diuretic dosage; other prescribed medications and their corresponding dosages; the patient's medical history including any previously prescribed medications and dosages; and the patient's dry or benchmark weight. This type of EMR 26 data is made available to the algorithm 24 as it may impact the selection of an appropriate diuretic dosage.

The following section will provide some specific examples of how EMR 26 data may be implemented by the algorithm 24 to select an appropriate diuretic dosage. EMR 26 information pertaining to other prescribed medications and their corresponding dosages may be relevant because the drug interaction may alter the effectiveness of diuretic medications. The patient's medical history including any previously prescribed medications and dosages may be relevant if, for example, the medical history reveals an atypical sensitivity to or tolerance of certain diuretic medications. The patient's dry or benchmark weight can be used to identify a sudden weight gain, which may be indicative of a pathological edema and may require a diuretic dosage increase.

The evidence-based guidelines 28 include a comprehensive set of instructions adapted to guide decisions in specific areas of healthcare. According to one embodiment, the guidelines 28 are transferred to the algorithm 24 in certain instances to define or supplement the logic on which a diuretic dosage recommendation is based. According to another embodiment, the guidelines 28 are directly incorporated into the algorithm 24 such that the algorithm 24 itself reflects the logic of the guidelines 28. For purposes of this disclosure, the term "logic" can be defined to include the specific manner in which the algorithm 24 evaluates input data for purposes of generating diuretic dosage recommendations.

Figure 2:
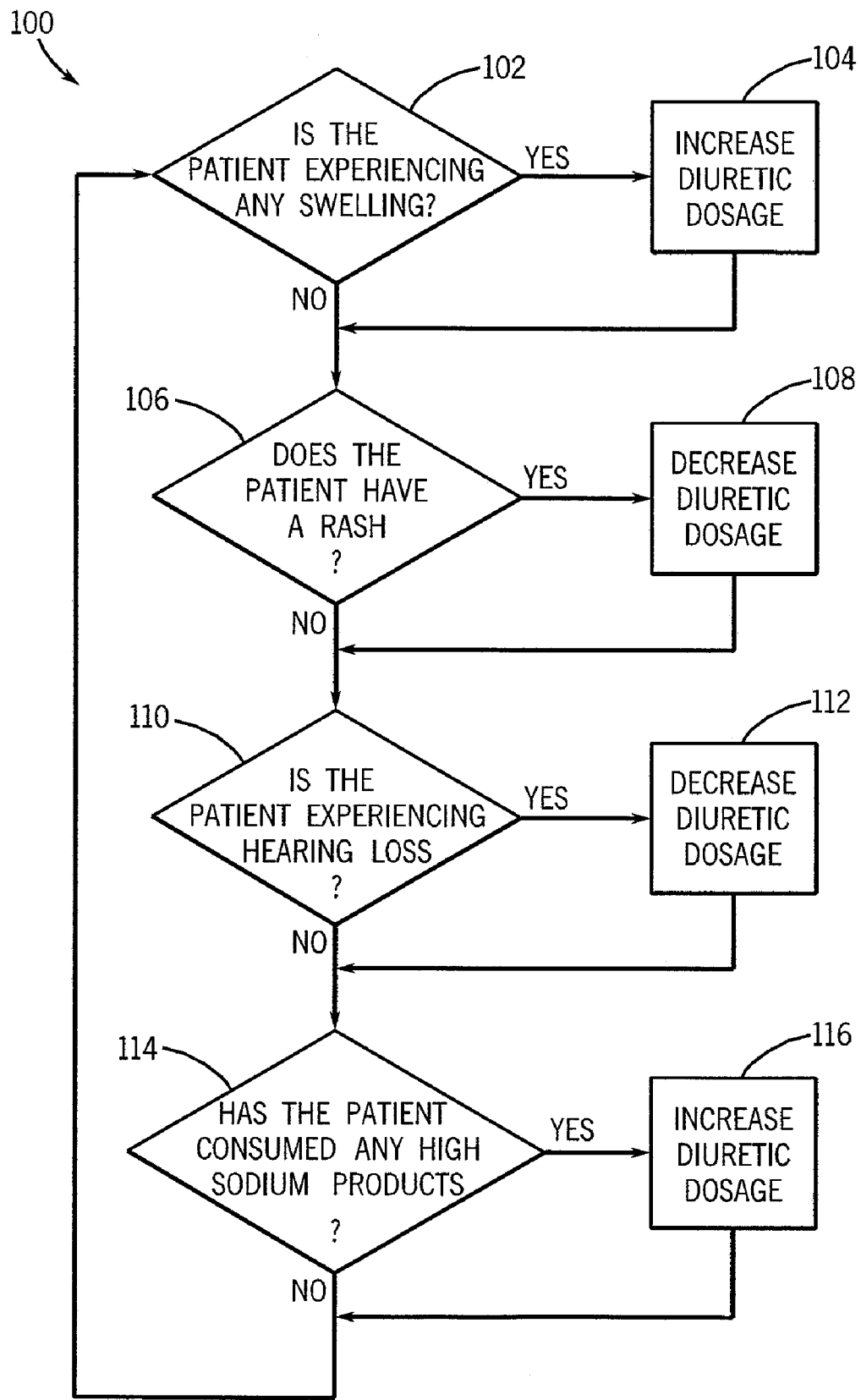
FIG. 2 is a block diagram illustrating an exemplary algorithm of the titration system of FIG. 1.
Figure 3:
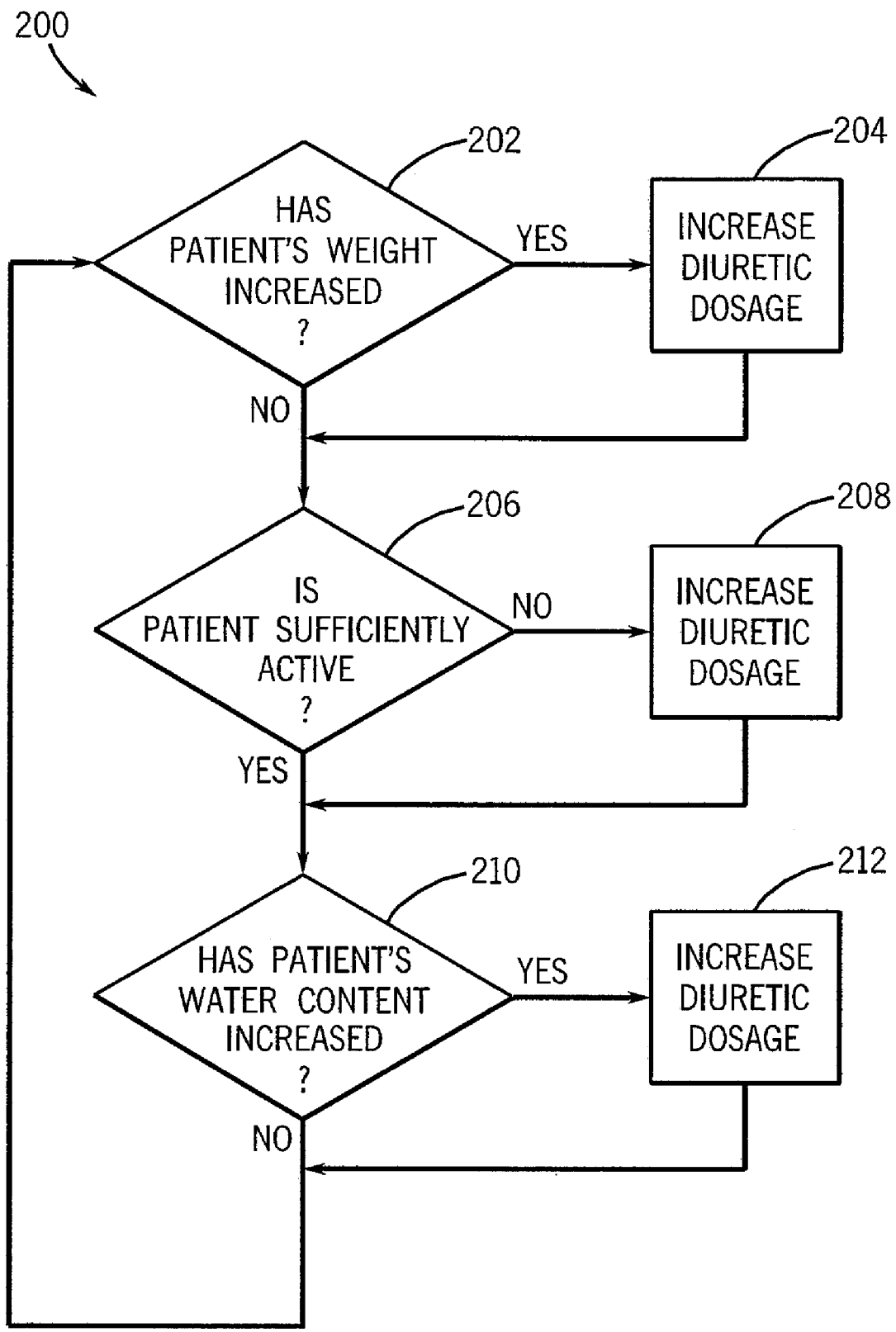
FIG. 3 is a block diagram of an exemplary algorithm for providing a diuretic dosage recommendation in response to input from the monitoring device of FIG. 1.

The algorithm 24 may comprise a variety of different forms of logic configured to evaluate input data in accordance with any known methodology for providing diuretic dosage recommendations. As an example, the algorithm 24 may incorporate logic from and provide diuretic dosage recommendations based on previously conducted medical research, the evidence-based guidelines 28, and/or a physician's personal experience with a given patient. FIGS. 2-3 provide more specific examples of methods that may be incorporated into the algorithm 24 in order to provide an appropriate diuretic dosage recommendation.

Referring to FIG. 2, a flow chart illustrates a method 100 for providing a diuretic dosage recommendation in response to input from the communication device 16 (shown in FIG. 1). The individual blocks of the flow chart represent steps that may be performed in accordance with the method 100. Unless otherwise specified, the steps 102-116 need not be performed in the order shown.

At step 102, the method 100 evaluates input from the communication device 16 (shown in FIG. 1) to determine if the patient 12 (shown in FIG. 1) is experiencing any swelling. If at step 102 the patient 12 is experiencing swelling, the method 100 proceeds to step 104 wherein the diuretic dosage is increased. After step 104, the method 100 proceeds to step 106. If at step 102 the patient 12 is not experiencing swelling, the method 100 proceeds directly to step 106.

At step 106, the method 100 evaluates input from the communication device 16 (shown in FIG. 1) to determine if the patient 12 (shown in FIG. 1) has a rash. If at step 106 the patient 12 has a rash, the method 100 proceeds to step 108 wherein the diuretic dosage is decreased. After step 108, the method 100 proceeds to step 110. If at step 106 the patient 12 does not have a rash, the method 100 proceeds directly to step 110.

At step 110, the method 100 evaluates input from the communication device 16 (shown in FIG. 1) to determine if the patient 12 (shown in FIG. 1) is experiencing hearing loss. If at step 106 the patient 12 has hearing loss, the method 100 proceeds to step 112 wherein the diuretic dosage is decreased. After step 112, the method 100 proceeds to step 114. If at step 110 the patient 12 does not have hearing loss, the method 100 proceeds directly to step 114.

At step 114, the method 100 evaluates input from the communication device 16 (shown in FIG. 1) to determine if the patient 12 (shown in FIG. 1) has recently consumed any high sodium products. If at step 114 it is determined that the patient 12 has recently consumed a high sodium product, the method 100 proceeds to step 116 wherein the diuretic dosage is increased. After step 116, the method 200 returns to step 102. If at step 114 it is determined that the patient 12 has not consumed any high sodium products, the method 100 returns to step 102.

Referring to FIG. 3, a flow chart illustrates a method 200 for providing a diuretic dosage recommendation in response to input from the monitoring device 18 (shown in FIG. 1). The individual blocks of the flow chart represent steps that may be performed in accordance with the method 200. Unless otherwise specified, the steps 202-212 need not be performed in the order shown.

At step 202, the method 200 evaluates input from the monitoring device 18 (shown in FIG. 1) to determine if the patient 12 (shown in FIG. 1) has gained weight. If at step 202 the patient 12 has gained weight, the method 200 proceeds to step 204 wherein the diuretic dosage is increased. After step 204, the method 200 proceeds to step 206. If at step 202 the patient 12 has not gained weight, the method 200 proceeds directly to step 206.

At step 206, the method 200 evaluates input from the monitoring device 18 (shown in FIG. 1) to determine if the patient 12 (shown in FIG. 1) has been sufficiently active. If at step 202 the patient 12 has not been sufficiently active, the method 200 proceeds to step 208 wherein the diuretic dosage is increased. After step 208, the method 200 proceeds to step 210. If at step 206 the patient 12 has been sufficiently active, the method 200 proceeds directly to step 210.

At step 210, the method 200 evaluates input from the monitoring device 18 (shown in FIG. 1) to determine if the water content of the patient 12 (shown in FIG. 1) has increased. If at step 202 the patient's water content has increased, the method 200 proceeds to step 212 wherein the diuretic dosage is increased. After step 212, the method 200 returns to step 202. If at step 210 the patient's water content has not increased, the method 200 returns to step 202.

At steps 104, 108, 112 and 116 of FIG. 2, and steps 204, 208 and 212 of FIG. 3, the magnitude and rate at which dosage is increased or decreased may, for example, be predicated on information from the EMR 26 (e.g., the patient's weight, sex, etc.) and on information from the evidence based guidelines 28 (shown in FIG. 1). Limits corresponding to maximum diuretic dosages, and maximum rates for increasing and decreasing diuretic dosages may be established as a precautionary measure.

Additional logic may be incorporated into the algorithm 24 to address conflicting dosage recommendations from steps 104, 108, 112 and 116 of FIG. 2, and steps 204, 208 and 212 of FIG. 3. For example, if the patient is experiencing swelling and is also experiencing hearing loss, steps 104 and 112 may respectively recommend both an increase and a decrease in diuretic dosage. The algorithm 24 may be configured to address conflicting dosage recommendations, for example, by assigning greater weight to one of the symptoms or by assessing the severity of the symptoms such that only one recommendation is ultimately conveyed to the patient 12. According to another embodiment, a healthcare provider such as the clinician 30 can be alerted when there are conflicting dosage recommendations so that the healthcare provider can evaluate the underlying information and make an appropriate recommendation.

Referring again to FIG. 1, after establishing a diuretic dosage recommendation, the algorithm 24 can convey such recommendation to the remotely located patient 12 via the communication device 16. According to an embodiment wherein the communication device 16 includes a telephone, the algorithm 24 may be configured to call the patient 12 and verbally convey a recommendation to either increase or decrease diuretic dosage. According to an embodiment wherein the communication device 16 includes a computer, the algorithm 24 may be configured to send the patient 12 an e-mail conveying the recommendation to either increase or decrease diuretic dosage.

According to another embodiment, the dosage recommendation and any data on which the recommendation is based may initially be conveyed to the clinician 30. Thereafter, the clinician 30 has the opportunity to evaluate and override the recommendation before it is conveyed to the patient 12. While the clinician 30 is depicted as being within the hospital 22, it should be appreciated that the clinician 30 may also be remotely located. As an example, the algorithm 24 may convey a dosage recommendation to a remotely located clinician via a cell phone or PDA. Thereafter, the remotely located clinician can call or otherwise contact the patient 12 if a dosage modification is appropriate.

The diuretic titration system 10 can provide an optimal diuretic dosage for each patient without requiring office visits or any other form of direct supervision. Therefore, remotely located patients can receive a high level of care and avoid potentially costly exacerbation of the disease. Additionally, as the diuretic titration system 10 is at least partially automated, a single clinician 30 can conveniently monitor a large number of patients without having to physically visit each one.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

I claim:

1. A diuretic titration system for use with a patient, comprising:
    a server located remotely from the patient and including an algorithm;
    a communication device operatively connected to the server, the communication device configured to generate condition specific inquiries to the patient, receive responses from the patient to the inquiries, and provide the responses to the algorithm on the server; and
    a monitoring device operatively connected to the server to provide monitored parameters of the patient to the algorithm;
    wherein the algorithm is configured to evaluate the responses received from the patient through said communication device and the monitored parameters from said monitoring device in order to identify a plurality of symptoms and provide diuretic dosage recommendations for each of the symptoms,
    wherein the algorithm is configured to resolve conflicting diuretic dosage recommendations by either assigning greater weight to one of the symptoms or selecting the most severe symptom to develop a single, final diuretic dosage recommendation that is conveyed to the patient through the communication device.

2. The diuretic titration system of claim 1, further comprising an electronic medical record transferable to the algorithm, wherein the algorithm utilizes the electronic medical record for the patient to provide the final diuretic dosage recommendation to the patient.

3. The diuretic titration system of claim 1, further comprising an evidence based guideline transferable to the algorithm, wherein the algorithm implements the evidence based guideline to evaluate the obtained responses and the monitored parameters.

4. The diuretic titration system of claim 1, wherein the algorithm is configured to convey the final diuretic dosage recommendation to a clinician before conveying the final diuretic dosage recommendation to the patient.

5. The diuretic titration system of claim 1, wherein the communication device includes a telephone system having interactive voice response technology.

6. The diuretic titration system of claim 1, wherein the communication device includes a computer system.

7. The diuretic titration system of claim 1, wherein the monitoring device includes a device configured to weigh the patient.

8. The diuretic titration system of claim 1, wherein the monitoring device includes a device configured to monitor patient motion.

9. The diuretic titration system of claim 1, wherein the monitoring device includes a device configured to monitor patient water content.

10. A diuretic titration system for use with a patient, comprising:
    a server located remotely from the patient and including an algorithm;
    a communication device operatively connected to the server, the communication device configured to generate condition specific inquiries to the patient, receive responses from the patient to the inquiries, and provide the responses to the algorithm on the server;

a monitoring device operatively connected to the server to provide monitored parameters of the patient to the algorithm;

an electronic medical record transferable to the algorithm; and an evidence based guideline transferable to the algorithm;

wherein the algorithm is configured to evaluate the responses received from the patient through said communication device, said monitored parameters from the monitoring device, said electronic medical record, and said evidence based guideline in order to identify a plurality of symptoms and provide diuretic dosage recommendations for each of the symptoms, wherein the algorithm is configured to resolve conflicting diuretic dosage recommendations by either assigning greater weight to one of the symptoms or selecting the most severe symptom to develop a single, final diuretic dosage recommendation that is conveyed to the patient through the communication device.

11. The diuretic titration system of claim 10, wherein the algorithm is configured to convey the final diuretic dosage recommendation to a clinician before conveying the final diuretic dosage recommendation to the patient.

12. The diuretic titration system of claim 10, wherein the communication device includes a telephone system having interactive voice response technology.

13. The diuretic titration system of claim 10, wherein the communication device includes a computer system.

14. The diuretic titration system of claim 10, wherein the monitoring device includes a device configured to weigh the patient and a device configured to monitor patient motion.

15. A method for monitoring and regulating the dosage of a diuretic medication administered to a remotely located patient comprising:

providing a communication device to generate condition specific inquiries to the patient and obtain responses from the patient;

providing a monitoring device to obtain condition specific monitored parameters from the patient;

transferring the obtained responses and the monitored parameters to an algorithm operating on a server located remotely from the patient;

implementing an algorithm on the server to evaluate said obtained responses and monitored parameters to identify a plurality of symptoms and provide diuretic dosage recommendations for each of the symptoms;

resolving conflicting diuretic dosage recommendations by either assigning greater weight to one of the symptoms or selecting the most severe symptom to develop a single, final diuretic dosage recommendation; and conveying the single, final diuretic dosage recommendation to the remotely located patient through the communication device.

16. The method of claim 15, further comprising conveying the final diuretic dosage recommendation to a clinician before said conveying the final diuretic dosage recommendation to the remotely located patient.

17. The method of claim 15, further comprising the step of obtaining patient information from an electronic medical record and utilizing the obtained patient information in the algorithm to provide the final diuretic dosage recommendation.

18. The method of claim 15, further comprising the step of implementing an evidence based guideline for purposes of evaluating said obtained responses and monitored parameters.

* * * * *